(12) United States Patent
Henderson et al.

(10) Patent No.: US 6,251,658 B1
(45) Date of Patent: Jun. 26, 2001

(54) INERTIAL IMPACT DRILL FOR CYTOLOGICAL APPLICATIONS

(75) Inventors: David A. Henderson, Farmington; John C. Fasick, III, Lima; Robert L. Culhane, Manchester; Edward H. Friedrich, Canandaigua, all of NY (US)

(73) Assignee: Burleigh Instruments, INC, Fishers, NY (US)

( * ) Notice: Subject to any disclaimer, the term of this patent is extended or adjusted under 35 U.S.C. 154(b) by 0 days.

(21) Appl. No.: 09/593,473

(22) Filed: Jun. 14, 2000

Related U.S. Application Data

(60) Provisional application No. 60/140,014, filed on Jun. 18, 1999.

(51) Int. Cl.[7] .................................................... C12M 1/00

(52) U.S. Cl. .......................... 435/285.1; 310/36; 310/328

(58) Field of Search ........................... 435/285.1; 310/36, 310/37, 328, 329

(56) References Cited

U.S. PATENT DOCUMENTS

| | | | |
|---|---|---|---|
| 3,835,338 | 9/1974 | Martin | 310/8 |
| 4,894,579 | 1/1990 | Higuchi | 310/328 |
| 5,225,750 | 7/1993 | Higuchi | 318/280 |
| 5,229,679 | 7/1993 | Higuchi | 310/328 |

FOREIGN PATENT DOCUMENTS

| | | |
|---|---|---|
| 03166079A | 7/1991 | (JP) . |
| 04041187A | 2/1992 | (JP) . |
| 04207982A | 7/1992 | (JP) . |
| 0690770 | 4/1994 | (JP) . |

OTHER PUBLICATIONS

Roland Hengstenberg, A Piezoelectric Device to Aid Penetration of Small Nerve Fibers with Microelectrodes, Journal of Neuroscience Methods, 4 (1981), pp. 249–255.

(List continued on next page.)

*Primary Examiner*—David A. Redding
(74) *Attorney, Agent, or Firm*—M. Lukacher

(57) ABSTRACT

An inertial impact drill for diverse applications in cytology such as in-vitro fertilization, genetic research, pharmaceutical research, cloning, etc., is designed to operate in conjunction with micropipettes, microelectrodes, and micromanipulators. The drill includes two opposing actuators, one version of which is comprised a plurality of individual piezoelectric elements, the other version is comprised of a plurality of electrostrictive elements. The actuators drive a small inertial mass to produce sharp short reciprocal movements of this mass. The movements of the inertial mass result in repetitive impacts that are transferred to the micropipette or a microelectrode, which is mechanically coupled to the body of the inertial impact drill. In addition, the impacts cause mechanical oscillation of the tip of a micropipette or a microelectrode at its resonant frequency that is higher than the repetition rate of the impacts. The drill is suitably attached to a micromanipulator that serves to advance in a controlled mode the drill toward a cell or withdraw it from the cell. Though no net displacement of the tip of the micropipette or the electrode is produced due to the action of the drill, the tip of the micropipette or of an electrode penetrates the wall/membrane of the cell and, if appropriate, that of the nucleus. Such penetration occurs without any damage to the cell or its nucleus. The cell is held in place in the usual manner with a holding pipette. The resulting opening may then be used to inject or remove sperm or other genetic, biological, or chemical materials into the cell or the nucleus, or to insert a microelectrode. The opening in the cell wall subsequently closes. The action of the inertial impact drill is like that of a miniature jackhammer.

24 Claims, 9 Drawing Sheets

OTHER PUBLICATIONS

T. Higuchi, Innovative Actuators for Micromanipulation and Microinjection in Biotechnology, Automation in Biotechnology Proceedings of the 4th Toyota Conference, Oct. 21–24, 1990, 1991 Elsevier Science Publishers B.V. pp. 145–157.

PMM PRIMA Piezo Micro Manipulator Brochure, Prima Meat Packers, Ltd., no date.

PMM Piezo Micro Manipulator Brochure, Prime Tech, Ltd., no date.

MP–31 Piezoelectric Vibration Device Instruction Manual, Narishige Co., Ltd., no date.

LSS–1000 Inchworm Microdrive System Brochure, Burleigh Instruments, Inc., no date.

High Speed Piezoelectric Positioning Systems (LSS–2000) Brochure, Burleigh Instruments, Inc., no date.

W.J. Lederer, "Piezoelectric Translator. A Simple and Inexpensive Device to Move Microelectrodes and Micropipettes Small Distances Rapidly" (Pflugers Archives, vol. 399, No. 1, Sep. 1983, pp. 83–86).

INERTIAL IMPACT DRILL FOR CYTOLOGICAL APPLICATIONS

This application claims the priority benefit of our U.S. Provisional application, Ser. No. 60/140,014, filed Jun. 18, 1999.

DESCRIPTION

1. Field of Invention

This invention relates to an inertial impact drill, and is especially suitable for use in cytological applications, as a clinical or scientific instrument for making microscopic holes in biological tissue.

It is a feature of this invention to provide an instrument that is able to puncture a cell wall with ease and enter the cell with a minimum damage thereby to preserve its viability.

2. Background

There is an increasing need for being able to inject into biological cells and their nuclei, genetic and other materials. Such procedures are used in cloning, in-vitro fertilization, genetic research, and in developing methods for treating cancer and genetically caused diseases. During procedures of this type a micropipette is used, guided by a micromanipulator, to penetrate the cell wall and in many cases then to enter the cell nucleus. In scientific experiments involving biological cells, microelectrodes are also frequently used to measure changes of electrical potentials or to apply electrical potentials to a cell.

Many methods and instruments are available now to facilitate cell wall puncture. All of them involve micromanipulators, which are used to force the tip of the micropipette through the cell wall. Some of these methods tend to severely deform the cell and frequently to cause damage, making the cell unusable for a particular task. Furthermore, the use of some of these instruments requires considerable skill. Representative examples of such methods and instruments may be found in the following patents and literature.

U.S. Pat. No. 3,835,338 of Sep. 10, 1974 discloses an electrically controlled ultra-micromanipulator that utilizes three sets of electrostrictive actuators orthogonally arranged to move and position a probe in small incremental steps.

U.S. Pat. No. 4,894,579 of Jan. 16, 1990 describes apparatus that uses a piezoelectric/electrostrictive element driving an inertia member to produce, through inertia, a fine net incremental displacement of a moving member.

U.S. Pat. No. 5,225,750 of Jul. 6, 1993 discloses a device that uses a piezoelectric or an electrostrictive element to generate rotary motion to, in turn, drive a plunger in controlled very small steps. The plunger moves a liquid to be injected through a microsyringe.

U.S. Pat. No. 5,229,679 of Jul. 20, 1993 describes a micromanipulator for biological applications that uses piezoelectric or electrostrictive actuators to drive an inertial mass to control, through impact, the incremental displacement of an aim in very small steps, facilitating the positioning in three axes of a miniature instrument attached to the arm. In the cases of using the device to puncture cell walls, the arm with the miniature instrument, e.g., a micropipette, advances in small steps due to the impacts through the cell wall. As in all systems of this type the incremental forward motion may cause damage to the cell.

An article by T. Higuchi of the University of Tokyo, Japan ("Innovative Actuators for Micromanipulation and Microinjection in Biotechnology", Proc. of the 4th Toyota Conf., 21–24 October 1990, Elsevier Science Publishers, 1994).

Prime Tech, a Japanese company, sells the PMM micromanipulator device, which uses a piezoelectric element to produce fine linear incremental forward motion of a micropipette used for injection of materials into cells.

Narishige, another Japanese company, sells a micromanipulator in conjunction with a micropipette to inject matter into biological cells. The device generates vibration using ultrasonic vibration for the penetration of the cell wall as the micromanipulator moves the micropipette forward.

Japanese patent, Publication Number 03166079 A (1991) discloses a means for eliminating vibration at the tip of a micro-instrument driven by a piezoelectric element and for micro-motion of this instrument in a straight line.

Japanese patent, Publication Number 04207982 A (1992) describes a piezoelectrically actuated micro-motion device in which two orthogonally placed piezoelectric actuators are driven by sinusoidal voltages.

Japanese patent, Publication Number 04041187 (1992) shows apparatus similar to that of U.S. Pat. No. 5,229,679, with a foot pedal controller.

W J. Lederer in his paper "Piezoelectric translator. A simple and inexpensive device to move microelectrodes or micropipettes small distances rapidly" (Pflugers Archives, v. 399, No. 1, September 1983, pp. 83–6) describes the use of any piezoelectric buzzer in conjunction with a simple mechanism to provide a rapid linear displacement over a distance of up to 15 nm of microelectrodes or micropipettes.

R. Hengstenberg discusses in his article "A piezoelectric device to aid penetration of small nerve fibers with microelectrodes" (J. Neurosci. Methods, v. 4, no. 3, October 1981, pp 249–55) a means for quickly penetrating the cell walls by a rapid advance to insert microelectrodes.

Burleigh Instruments, Inc., of Fishers, N.Y., USA, sells a piezoelectric linear stepper motor, the LSS-1000 Inchworm® System, for positioning over a distance of many millimeters microelectrodes and micropipettes for in-vitro and n-vivo electrophysiological procedures. The Inchworm (U.S. Pat. Nos. 3,902,084 and 3,902,085) produces submicrometer size steps with high acceleration and high velocity that enables the tip for the microelectrode or micropipette to penetrate many millimeters of biological tissue. This device, however, may cause damage to cells, especially the ova, because it produces large indentations in cell walls.

Burleigh Instruments, Inc. also sells a piezo-electric actuator (the LSS-2000 Cell Penetrator System) for rapidly advancing microelectrodes and micropipettes in rapid programmable steps of up to 200 micrometers. This product has been successfully used, for example, to penetrate frog muscle fibers (Charleton and Robitaille, J. of Neuroscience, January "92, pp 297–305). However, this product does not work for cells that have thick walls, such as the ova.

All of these prior art devices achieve or facilitate penetration of cell walls by way of controlled net forward displacement of a micropipette or a microelectrode. Such displacement that forces the tip of the micropipette or microelectrode through the cell wall can lead to gross permanent distortion of cell wall with the resulting damage to the cell.

SUMMARY OF THE INVENTION

An inertial impact drill according to our invention facilitates the penetration of cell walls with a minimum damage by imparting inertial impact on the tip of an insertion element micropipette or a microelectrode without any net displacement of the tip. The smooth penetration is further facilitated by the mechanical oscillation of the tip of the micropipette or microelectrode at their resonant frequencies that are significantly higher than the repetition rate of the impact pulses. Any forward motion that might be required, as the cell wall is being gradually eroded to make an opening, is provided by a separate micromanipulator to which the drill is attached. In many cases the micromanipulator is only required to advance the assembly of the drill and the micropipette or the microelectrode sufficiently far to press the tip against the cell wall forming a small indentation. The impact action of the drill then erodes the cell wall generating an opening without further advancement by the micromanipulator. In the drill of the invention, actuators are energized by triangular electrical pulses that approximate impulses and thus are constituted of a fundamental frequency and a very large series of harmonics with frequencies greater than 1 KHz. Consequently, one of these harmonics will be close to the natural resonant frequency of the micropipettes or microelectrodes and thus will excite mechanical oscillation at the natural resonant frequency, which is higher than the repetition rate of the impulses.

Preferably the drill provided by the inventor has opposing actuators attached to opposite ends of an inertial mass. The actuators are biased with a dc voltage such that they are maintained at about one half of their maximum strain. In this manner two objectives are achieved: mechanical stability of the actuator-inertial mass assembly and also an increased stiffness of the assembly including the mass, actuators and insertion element. To bring about half-the-maximum strain on the actuators, the actuators are electrically connected in series between the source of dc reference voltage and the ground, as a result each stack is biased at approximately one half of the total dc reference voltage. The triangular electrical pulses are applied at an electrical junction between the two actuators. Thus when alternately positive and negative pulses are injected, the strain on one actuator stack is reduced, while the strain on the opposing actuator is increased causing a corresponding displacement of the inertial mass. In addition, the bodies of the actuators are mechanically preloaded to further facilitate the mechanical stability of the actuator-inertial mass assembly and an increased stiffness of the assembly.

Accordingly, one object of this invention is to provide an improved inertial impact drill which is adapted for the penetration of the walls of biological cells while minimizing damage to the cells.

Another object of this invention is to provide an improved inertial impact drill that incorporates two opposing actuators that move, when appropriate electrical signals are applied to them, an inertial mass situated between the actuators.

A further object of this invention is to provide an improved inertial impact drill in which the actuators are made of piezoelectric material.

Still further object of this invention is to provide an improved inertial impact drill in which the actuators are made of electrostrictive material.

Yet another object of this invention is to provide an improved inertial impact drill in which dynamic forces of an inertial mass are transferred to the body of the drill generating an impact or a series of impacts in the direction of the major axis of the body, the impacts being transferred to a micropipette or a microelectrode affixed to the body, such that no net displacement in the micropipette or microelectrode results.

An additional object of this invention is to provide an improved inertial drill driven by electrical signals having waveforms triangular in shape so as approximate impulse waveforms and therefore have a large number of harmonic frequencies greater than 1 KHz thus facilitating mechanical resonant oscillation of the tip of the micropipette or the microelectrode, at frequencies much higher then 1 KHz.

An additional object of this invention is to provide an improved inertial impact drill that comprises a drill mechanism and a driver/amplifier electrically connected to the drill mechanism.

A further object of this invention is to provide an improved inertial impact drill for making microscopic holes especially in cells or other biological tissues, which is affixed to a micromanipulator that provides for positioning, and displacement control of the drill.

Still another object of this invention is to provide an improved inertial impact drill having electrostrictive or piezoelectric actuators electrically connected in series and which have one contact of one of the actuators connected to a dc reference voltage, one contact of the second actuator connected to a common electrical ground, and the second electrical contacts of both actuators connected at a common point or junction.

Yet a further object of this invention is to provide an improved inertial impact drill in which two actuators, connected to an inertial mass, are driven by electrical pulses having triangular waveforms applied to a common point between the two actuators and drive the actuators, such that the actuators are driven simultaneously by the electrical pulses so as to achieve a brief net displacement of the inertial mass first in one direction then in the opposite direction.

Another object of this invention is to provide an improved drill per the preceding object in which the pulses have maximum amplitude equal to the magnitude of a dc reference voltage.

Still an additional object of this invention is to provide an improved inertial impact drill having electromechanical actuators connected to an inertial mass in which opposing forces are applied to the mass by electrically energizing the actuators at times occurring between pulses, driving the actuators to approximately one half of their maximum strain imparted to the actuators, to achieve a mechanical preload of the inertial mass in order to keep the actuators and bonds between the inertial mass and the actuators in constant compression to facilitate mechanical stability and increase stiffness of the actuator mass.

Another object of this invention is to provide an improved inertial impact drill per the preceding object in which preload is applied to the bodies of the actuators in order to further facilitate mechanical stability and increase stiffness thereof.

A further object of this invention is to provide an improved inertial impact drill having electromechanical actuators driven by pulses in which the total number in a series of inertial impacts is a function of the number of pulses applied to the actuators, the number of pulses being controlled by the drill operator.

Yet another object of his invention is to provide an improved inertial impact drill having an electromechanical actuator driven by pulses from a driver/amplifier in which the repetition rate, amplitude, and duration of the pulses can be controlled by the operator via the driver/amplifier, thus allowing the operator to optimize the efficiency of the penetration while minimizing damage to the object being penetrated by the drill, especially when that object is a cell.

A still further object of this invention is to provide an inertial impact drill per the preceding object in which the number of pulses in controllable by the operator using a foot pedal electrically connected to the driver/amplifier.

It should be understood that the invention is not restricted to achieving all of the objects set forth above, but only some of them.

Briefly described, an inertial impact drill in accordance with the inventor is adapted for use in conjunction with elements, such as micropipettes or microelectrodes in cytological applications to facilitate penetration of cell walls/membranes without causing permanent damage to the cells. The drill operates by producing impacts and also mechanical oscillation of the tips of the micropipettes or microelectrodes affixed to the body of the drill, but does not impart a net displacement at the tips. Displacement and positioning are provided separately by a micromanipulator to which the body of the drill is affixed.

DETAILED DESCRIPTION

Figure 1:
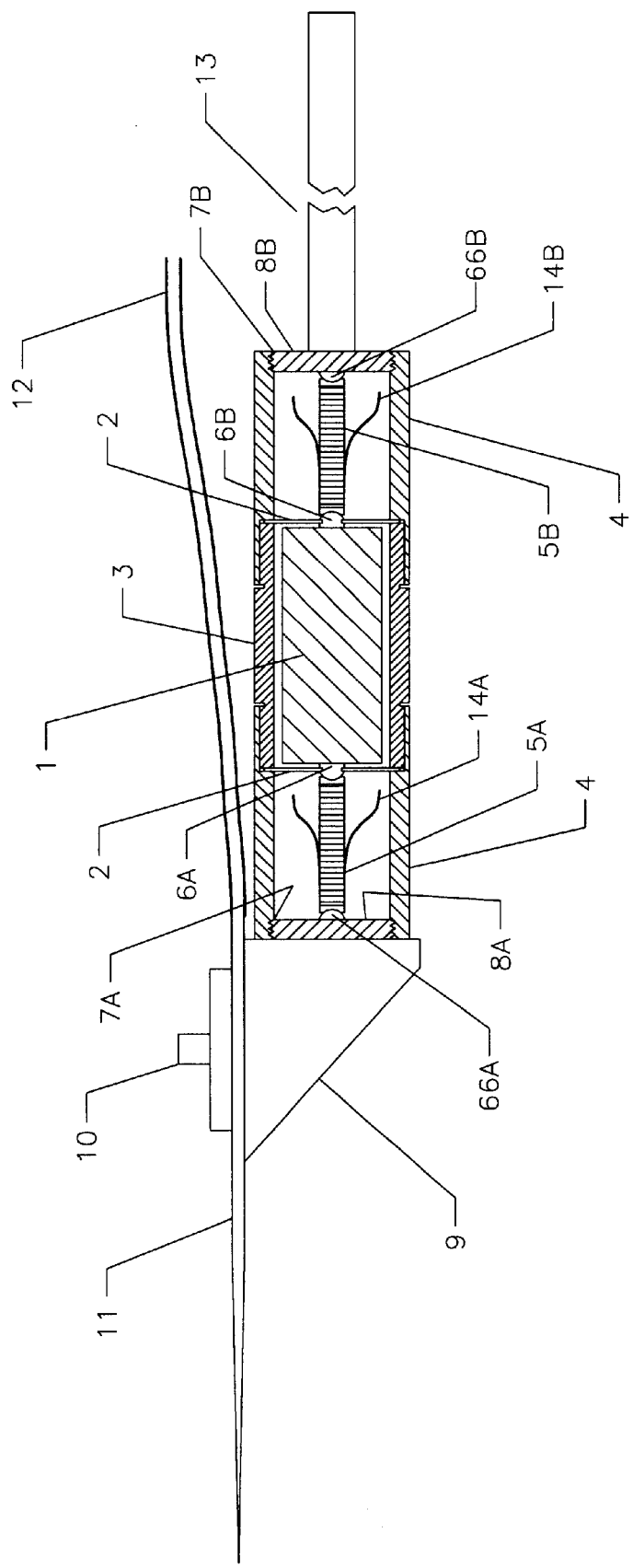
FIG. 1 is a side view which illustrates, schematically, the internal mechanism of an inertial impact drill, in accordance with the invention, having two opposing actuators and an inertial mass.
Figure 2:
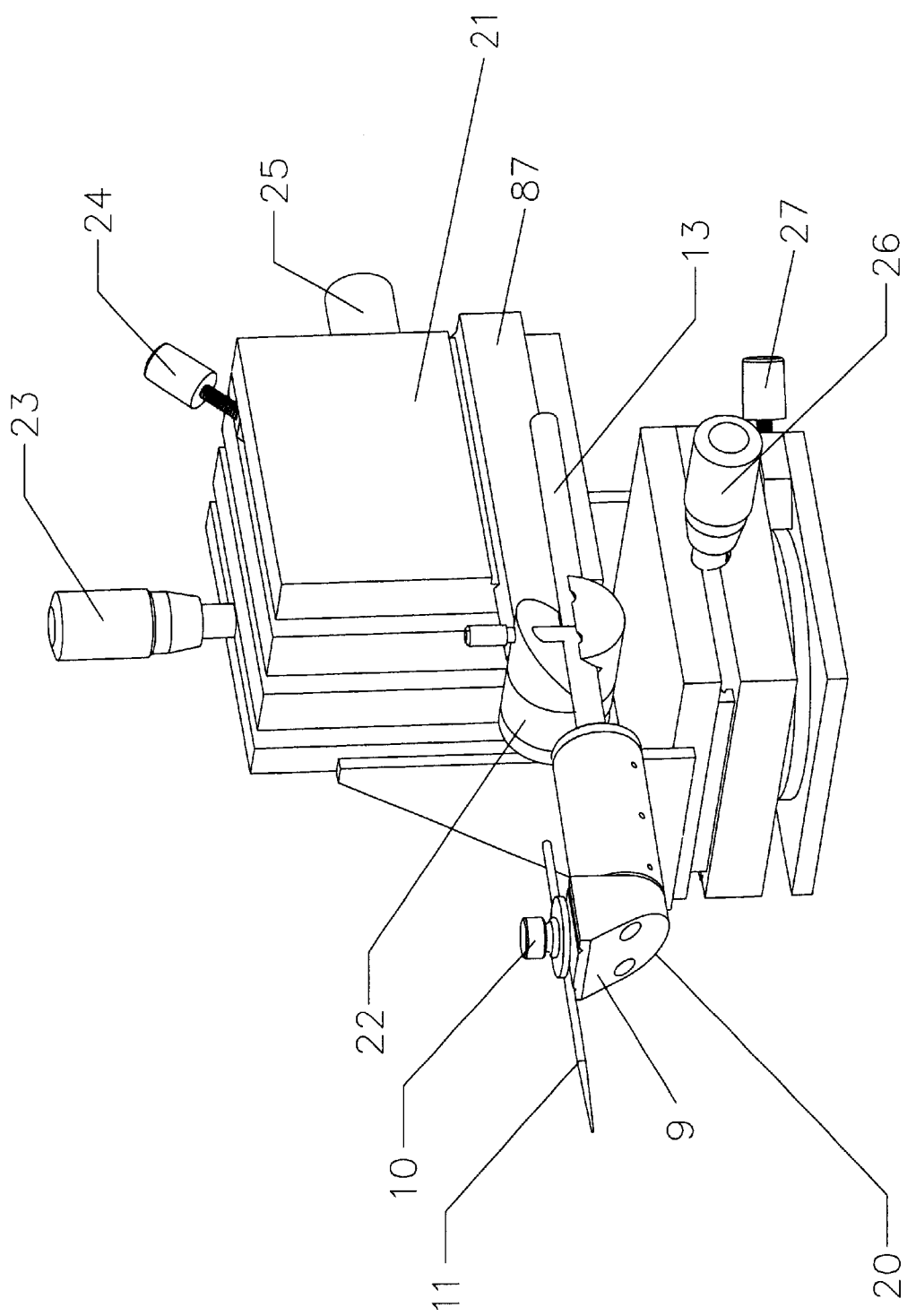
FIG. 2 is a perspective view which depicts the inertial impact shown in FIG. 1 mounted on the arm of a micromanipulator and holding the micropipette.

FIG. 1 shows the cross-section of the mechanism of the inertial impact drill 20 (which also appears in FIG. 2). The small cylindrical inertial mass 1 is located between to actuators 5A and 5B. The actuators can be made of piezoelectric material or electrostrictive material. No change would be required in the mechanism to accommodate either type. Because a dc reference voltage is applied to the actuators 5a and 5b through pairs of electrical conductors 14A and 14B to generate on these actuators approximately 50% of the maximum strain, the actuators press firmly against the hemispherical bosses 6A and 6B enhancing mechanical stability of the assembly comprising the actuators and the small inertial mass as well as increasing the stiffness of the assembly. Hemispherical bosses provide a single point axial contact for the actuators.

The inertial mass 1 is contained in the cylindrical outer center housing 3 and terminated on both ends by flexures 2. Bosses 6A and 6B passing through apertures in the flexures support the inertial mass in the center of the outer center housing 3. On the opposite ends of the actuators 5A and 5B, with respect to the inertial mass 1, the actuators are pressed against bosses 66A and 66B which are integral parts of the threaded end caps 8A and 8B. The assembly is also axially preloaded by the end caps that screw at 7A and 7B, into the outer end housing 4. The outer center housing 3, the outer end housing 4 and the end caps 8A and 8B comprise the body of the inertial impact drill. A holder block 9 is affixed to the body to support the an insertion element,micro-pipette 11, clamped to the holder 9 by the clamp 10. Instead of the micropipette 11, a microelectrode can be used. The entire mechanism of the inertial impact drill is affixed to the mounting rod 13.

As shown in FIG. 2 inertial impact drill 20 is mounted on micromanipulator 21, and held in place by clamp 22 by the mounting rod 13. Manual controls 23, 24, 25, 26, and 27 of the micromanipulator allow accurate pre-positioning of the tip of the micropipette or the microelectrode. When used with the inertial impact drill 20, after the prepositioning the manipulator serves to advance or retract the inertial impact drill including the micropipette 11 or a microelectrode with respect to the body (which is a biological tissue or cell-as seen in FIG. 4).

Figure 3:
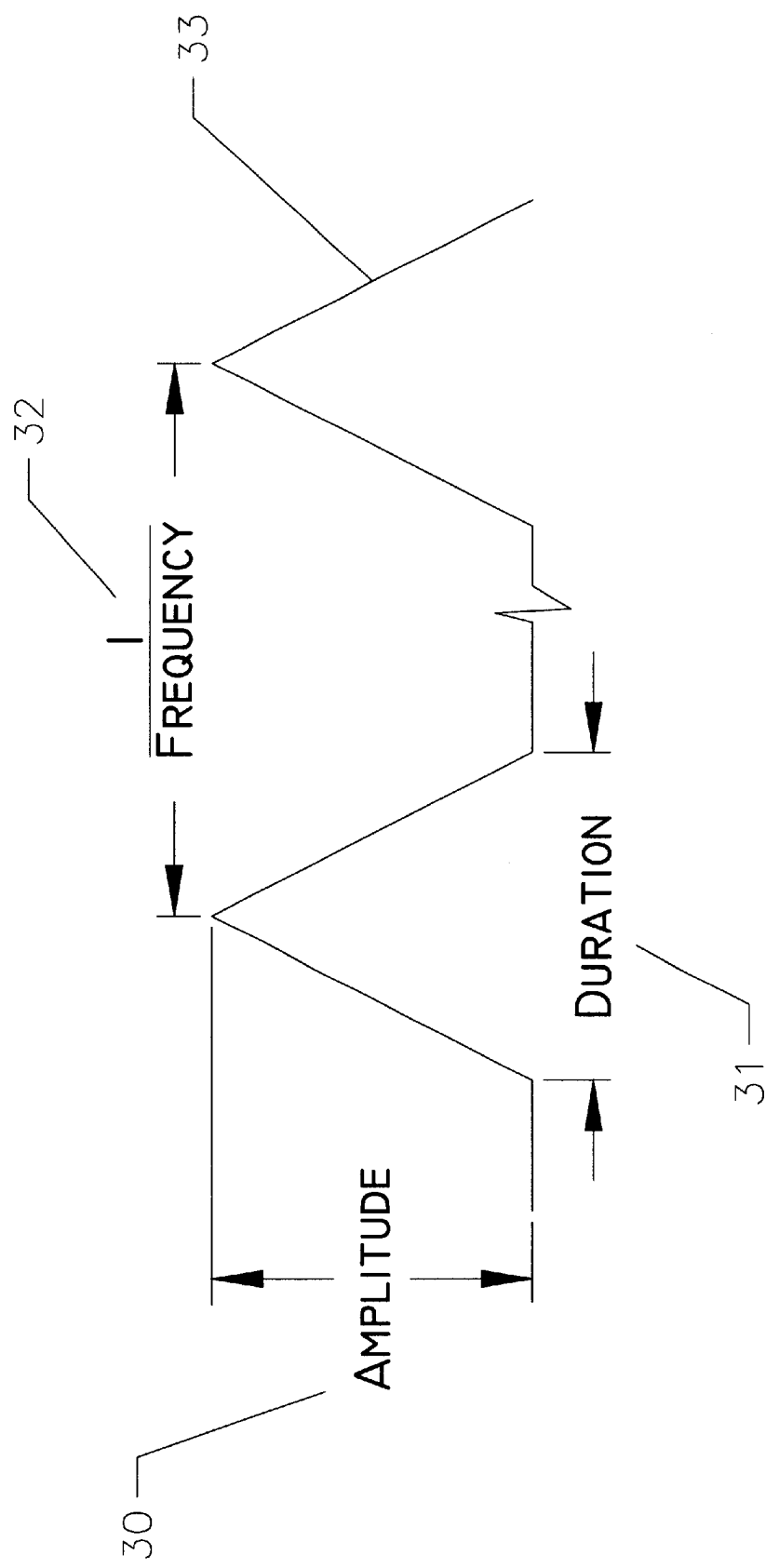
FIG. 3 shows a typical electrical pulse that drives the inertial impact actuator stack.

FIG. 3 shows the voltage pulses 33 that drive the actuators 5A and 5B. The amplitude A with respect to ground of the pulses is variable by the operator. C is the interval between the pulses equal to one over the pulse repetition rate, and B is the pulse width. The pulses are triangular in shape thus, in addition to the fundamental frequency determined by the pulse duration, the pulses are comprised of a large plurality of harmonics with frequencies greater than 1 KHz, which may be the repetition rate of the pulses. Consequently, when a pulse is applied to the actuators, the result is a sharp displacement of the inertial mass 1 producing an impact on the body of the inertial drill 20 and therefore on the micropipette 11 or the microelectrode, but the impact also generates a mechanical oscillation of the tip of the micropipette or the microelectrode at their resonant frequency that is equal to or close to one harmonics. This may be of the order of 10 KHz 20–KHz. Together the impact and the oscillation allow the tip of the micropipette or microelectrode, without net forward displacement, to penetrate a cell wall and, if appropriate, the nucleus membrane thereof with a minimum of damage to the cell. To achieve the penetration the tip of the micropipette or the microelectrode is brought by the micromanipulator 21 in intimate contact including slight pressure with the cell wall. No further forward motion is then needed for penetration.

Figure 4:
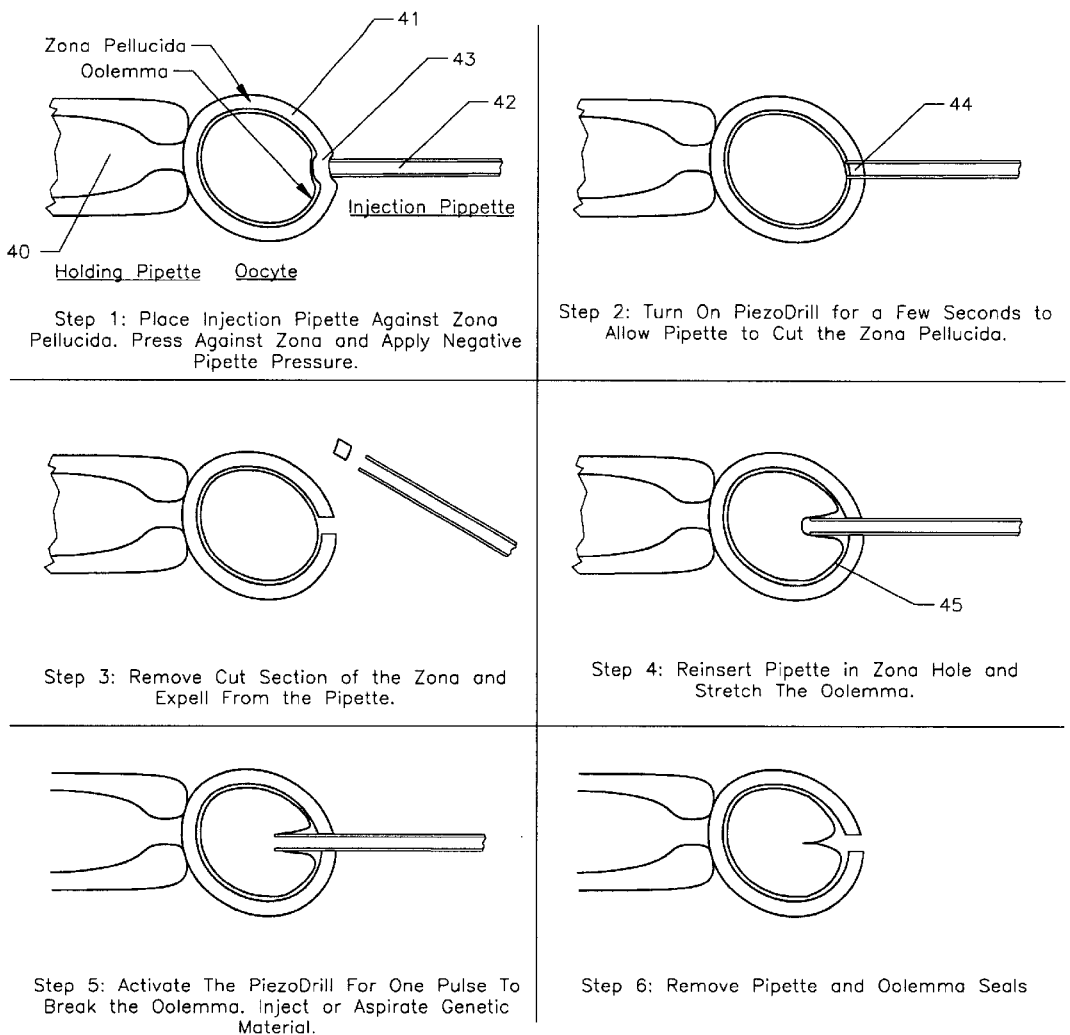
FIG. 4 schematically depicts six successive steps in the method of using the drill provided by the inventor in forming a hole in the wall of the biological cell held in place by holding pipette and being penetrated though its wall by an injection pipette.

FIG. 4 illustrates the penetration process. The cell 41, in this example an ovum, is being held in place in the usual manner by the holding pipette 40. In Step 1 the 42 of the micropipette 11 is brought by the micromanipulator 20 (not shown) into close contact with the zona pellucida (the cell wall) of the ovum causing a slight indentation 43. Due to impact transmitted to the tip of the micropipette from the body of the inertial impact drill and the mechanical oscillation of the tip and without any further net forward displacement of the tip 42. In Step 2 the zonapellucida is penetrated and a small cylindrical piece 44 is cut out of the zona pellucida. Step 3 shows how the tip 42 is withdrawn from the cell 41 and the cut out piece is discarded. In Step 4 the tip 42 is reinserted into the ovum and advanced forward until it touches the oolema (the membrane around the nucleus) producing a slight indentation. The tip then penetrates the oolema in the same manner as it has penetrated the zona pellucida as illustrated in Step 5. In Step 6 the tip is withdrawn after injecting a sperm, the oolema closes up, and the perforation in the zona pellucida soon also closes. The same procedure applies to other types of biological cells.

Figure 5:
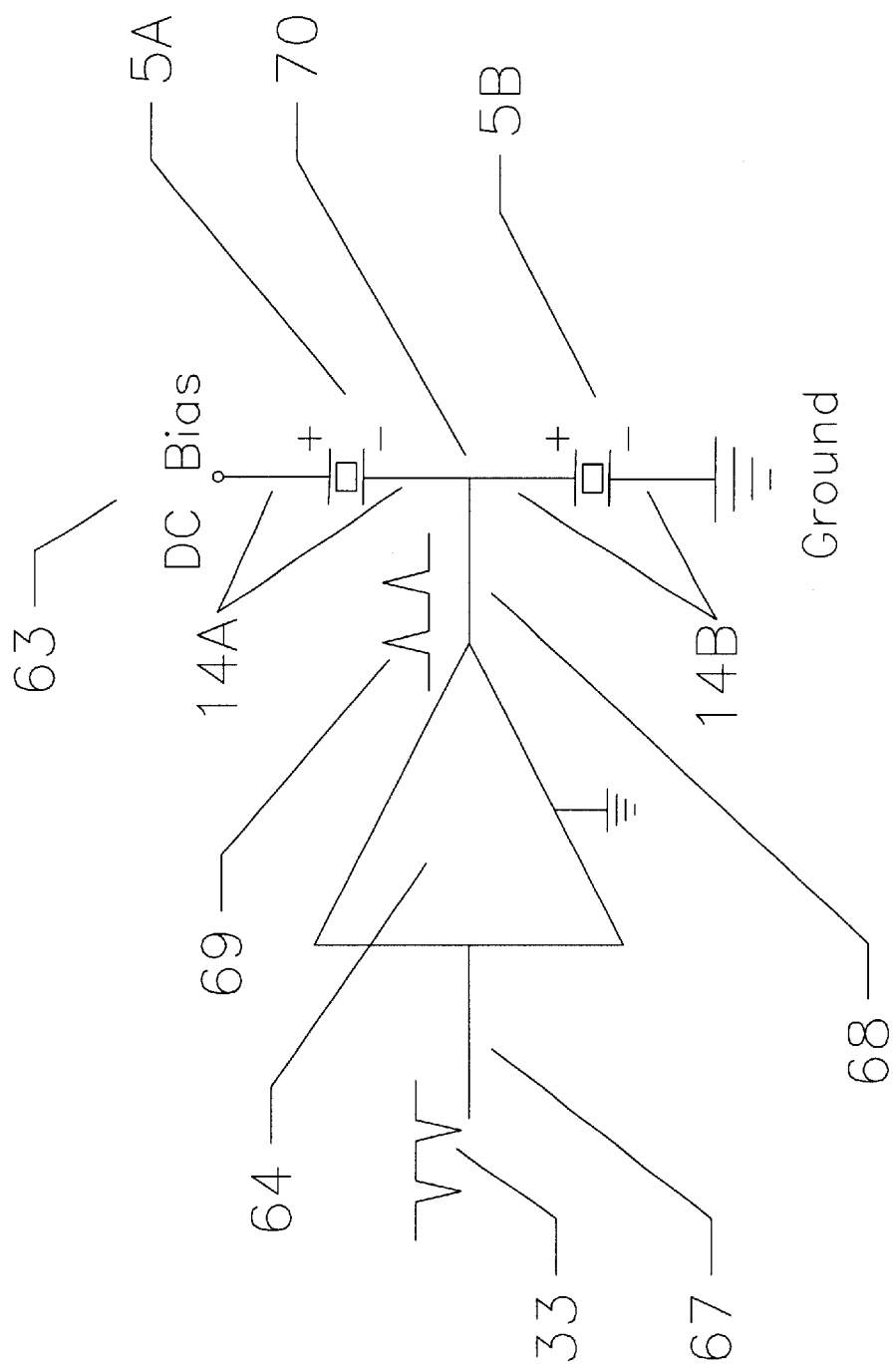
FIG. 5 is a schematic electrical diagram which illustrates the driver/amplifier which provides controlled electrical pulses for the drill.

FIG. 5 shows schematically the driver/amplifier circuit that drives the actuators 5A and 5B. An inverting broadband pulse amplifier 64 receives through its input terminal 67 pulses 33. The pulses are amplified such that the sum of the voltage drops across the two actuators is equal to the dc reference voltage. The pulses are output on terminal 68 connected to the common junction 70 of one each of the pairs of the electrical conductors 14A and 14B. The second electrical conductor of the conductor pair 14A is connected to the source of the dc reference voltage. The second electrical conductor of the conductor pair 14B is connected to the ground. The dc reference voltage has a magnitude sufficient to generate 50% of the maximum strain on the actuators 5A and 5B when no pulses are applied to the common junction 70.

When a pulse is applied to the common junction with the sum of the voltage drops across the two actuators equal to that of the magnitude of the dc reference voltage and the pulse is of the same polarity as the dc reference voltage, the voltage across the actuator 5A drops to zero while the voltage across the actuator 5B increases to the full value of the dc reference voltage. Consequently the actuator 5A is no longer strained while the actuator 5B is at its maximum strain. A displacement of the inertial mass 1 in the direction of the actuator 5A results. Between the pulses common junction 70 returns to ground, i.e. zero voltage, thus removing the strain from the actuator 5B and applying maximum voltage and causing maximum strain of the actuator 5A. This causes a displacement of the inertial mass in the direction of the actuator 5B. When a series of pulses is so applied, a repeated reciprocal motion of the inertial mass is generated producing impacts on the end caps 8A and 8B of the body of the inertial impact drill 20. These impacts are transmitted to the body of the inertial drill and therefore also to the micropipette or a microelectrode, in addition causing the resonant mechanical oscillation of the tips of the micropipette or microelectrode.

Figure 6:
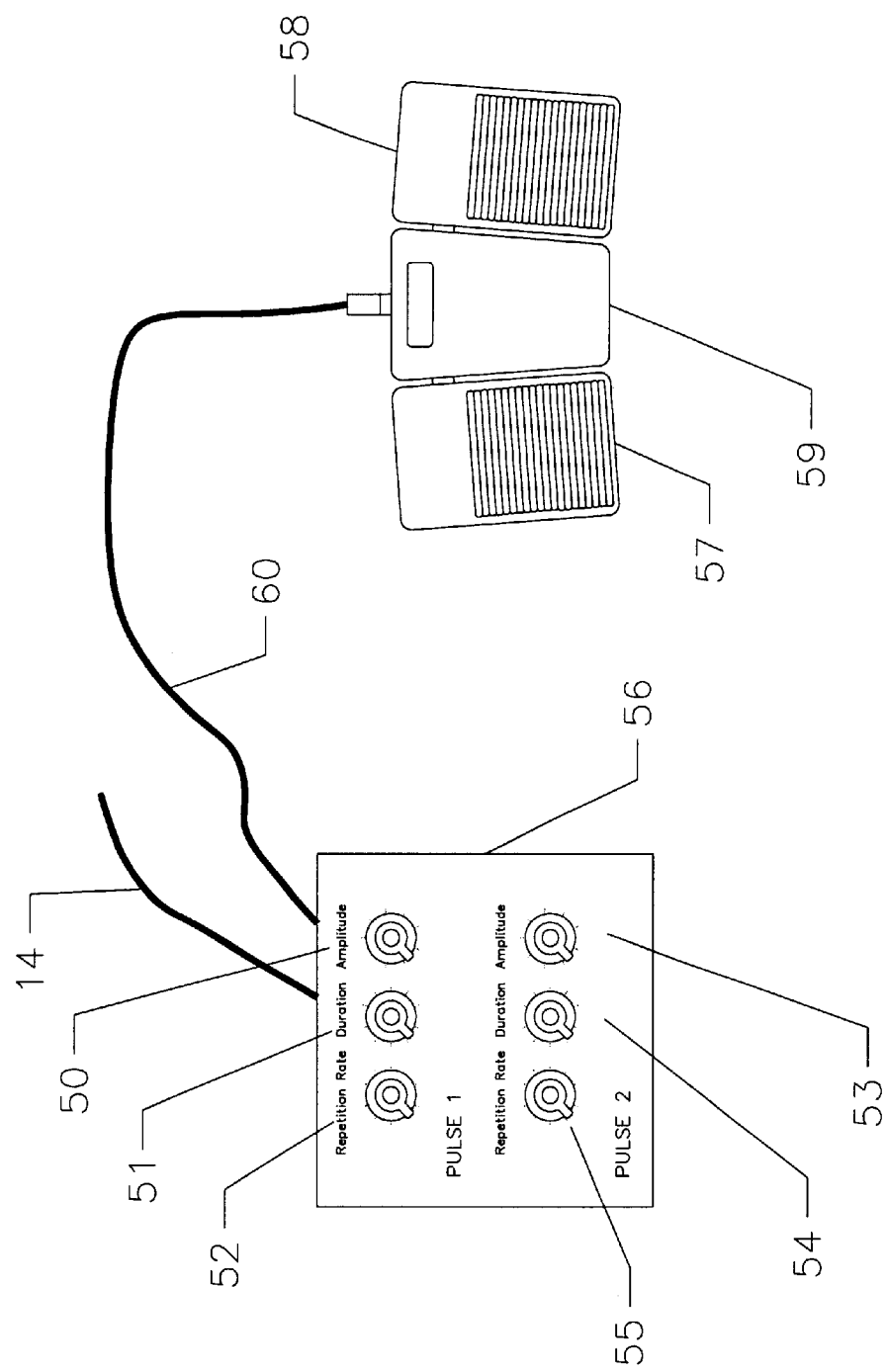
FIG. 6 is a block diagram of the controls for the drill.

FIG. 6 shows diagrammatically the control unit and power supply 56 and the foot pedals assembly 59 connected to the control unit by cable 60. A provision is made in the control unit 56 to separately control the repetition rate, pulse duration, and amplitude of two types of pulses, three controls for each type. Then the most appropriate pulse is selected using either foot pedal 57 or foot pedal 58. The duration of a pulse train depends on how long does the operator depress a foot pedal. Cable 14 containing two pairs of electrical conductors 14A and 14B.

Figure 7:
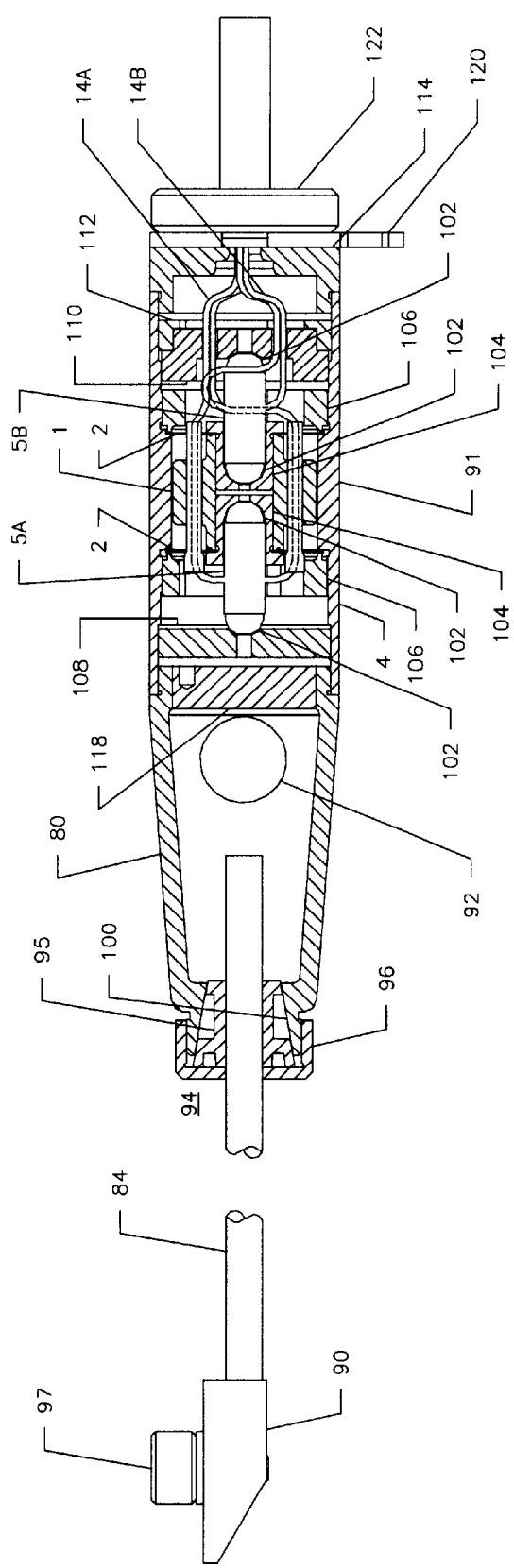
FIGS. 7 and 8 and 9, respectively, are a view similar to FIG. 1 and perspective views showing two other embodiments of the invention.
Figure 8:
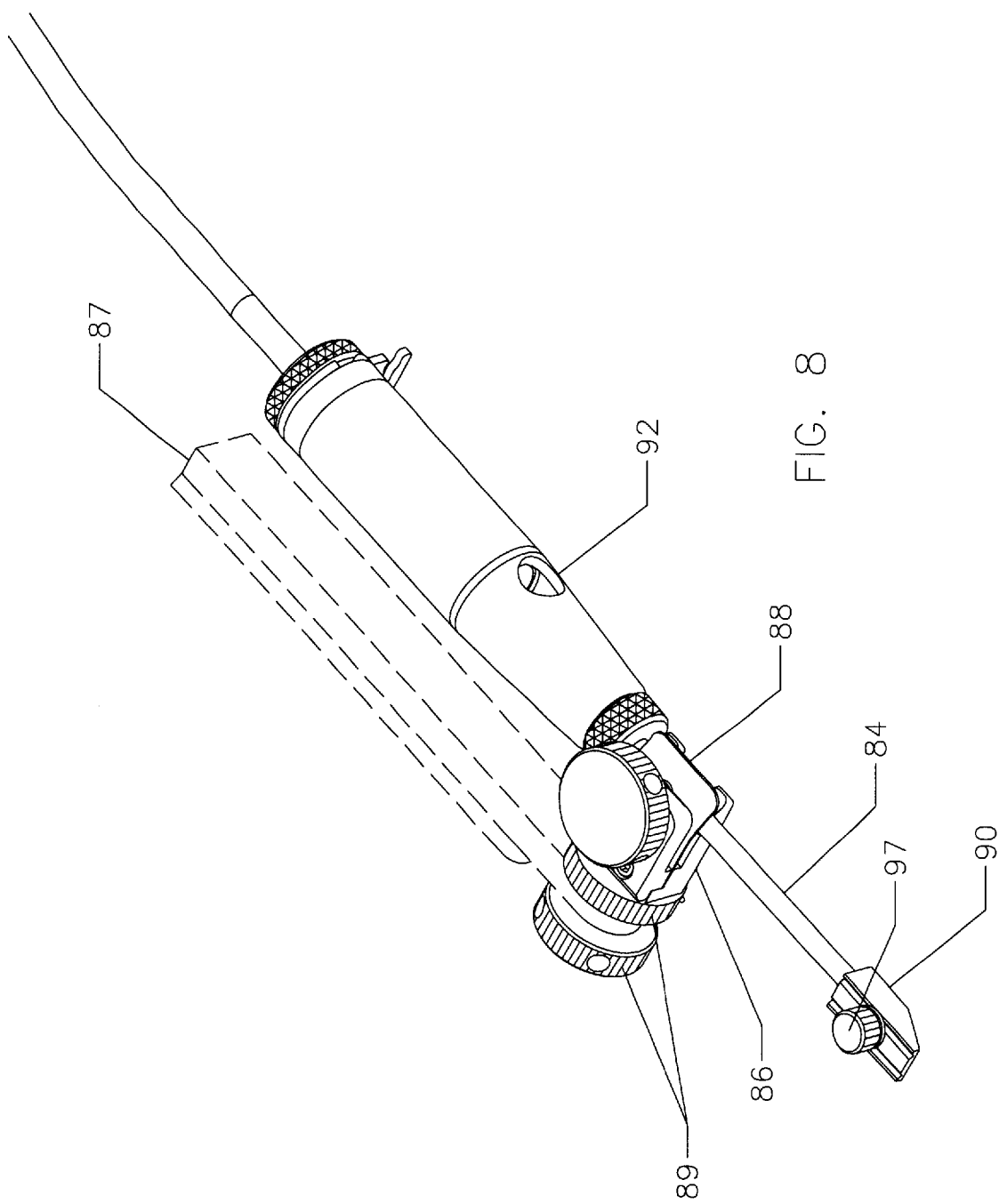

FIG. 7 shows a hollow cone adapter, also called a "snout", screwed onto the front of the housing 91 at its outer and 4, facilitates mounting of either a hollow shaft pipette holder or a solid shaft pipette holder 84. The pipette holder 4 is attached to the micromanipulator 21 along a side therof, by a clamp 86, which compresses a spring plate 88 against the holder (FIG. 8). Only a part 87 of the micromanipulator to which the clamp 86 is attached by threaded knobs 89 is shown in FIG. 8.

Figure 9:
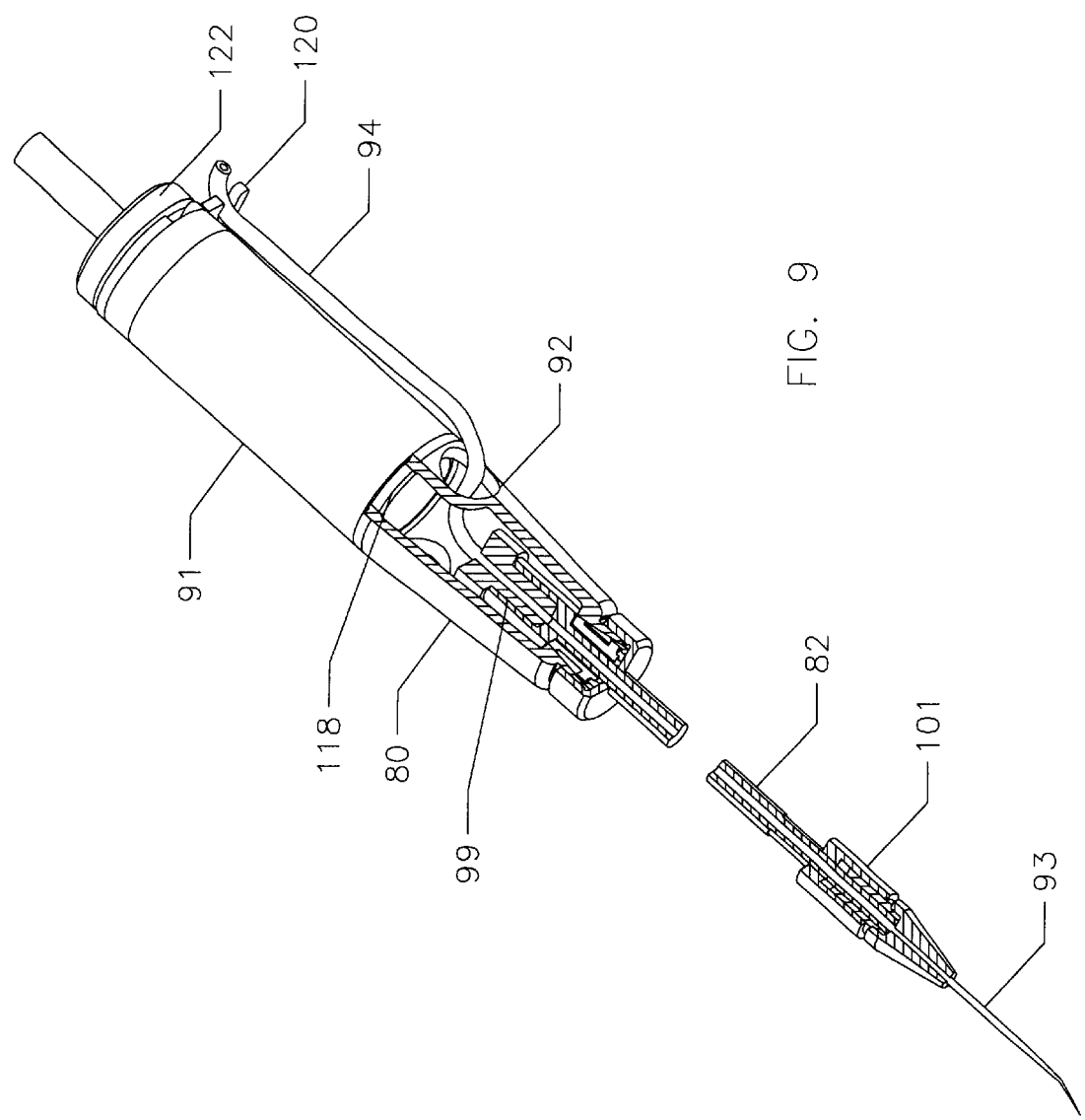

A hole 92 in the side of the cone adapter optionally (see FIG. 9) allows fluid delivery tube 94 to be fed into the snout 80 and thus into and through the hollow shaft t 82 to the pipette 93 located at the end of the shaft. The insertion element (not shown in FIG. 7) is attached to the solid rod holder 84 by a clamp 97 attached to a block 90 in a manner similar to that shown in FIG. 2. The hollow holder 82 is connected to the flexible fluid or suction tube 94 by a coaxial clamp 99 shown in FIG. 9. The pipette 93 is connected to the hollow holder 82 by a coaxial clamp 101.

The cone adapter 80 holds the solid or hollow pipette holder 84 or 82 forward of the housing 91, allowing for positioning of the pipette within the volume of a sample dish in a confined space. Additionally the cone adapter 80 acts to focus the pulse energy generated by the actuator, mass mechanism in housing 91, thus transmitting a clean axial pulse without cross coupling of lateral vibration. This enhances the performance and flexibility in manipulation of the drill.

The holders 82 or 84 are clamped at the exit 94 of the cone 80 by a collet mechanism 96 (a tapered shaft collet ring 95) in a reverse tapered opening 100 at the exit 94 of the cone 80. The holders are mounted coaxially with the axis along which the inertial mass 102 (the axis of the drill and cylindrical housing 91) which provides for efficient transmission of the mechanical pulses via the holders (82 or 84) to the pipettes, as mentioned above. A seal 118 protects the interior of the drill mechanism from contaminants. The drill (FIGS. 7–9) is of a design similar to shown in FIG. 1, but with the following difference.

The DC reference voltage applied to the actuators 5a and 5b through pairs of electrical conductors 14A and 14B generates on these actuators approximately 50% of the maximum strain. The hardened steel hemispherical bosses 102 glued to the end of the actuators press firmly into the inner clamps 104 enhancing mechanical stability of the assembly comprising the actuators 5A and 5B and the small inertial mass 1, as well as increasing the stiffness of the assembly. Hemispherical bosses 102 provide a single point axial contacts for the actuators 5A and 5B.

The inertial mass 1 is contained in the single cylindrical outer housing 91 and terminated on both ends by flexures 2. Inner clamps 104, passing through apertures in the flexures, support the inertial mass in the center of the outer housing 91. On the opposite ends of the actuators 5A and 5B, with respect to the inertial mass 1, the actuators are pressed into preload rings 108 and 110 captive within the cylindrical outer housing 91. The preload ring 108 on the opposite end of the forward actuator 5A axially preloads the assembly by screwing into the cylindrical outer housing. The preload ring 110 on the opposite end of the rear actuator 5B axially preloads the assembly as the locking ring 112 is screwed into the cylindrical housing securing the assembly. The hardened steel hemispherical bosses 102 glued to the end of the actuators press firmly into the preload rings 108 and 110 enhancing mechanical stability of the assembly comprising the actuators, the small inertial mass, and the cylindrical outer housing as well as increasing the stiffness of the assembly. The end cap 114 is screwed into the rear of the cylindrical outer housing 91 to seal the drill mechanism and protect it from contaminants. It also allows the electrical conductors 14A and 14B to exit through the rear of the cylindrical outer housing 91 so as not to interfere with positioning and operation. A tube holder 120 (see also FIG.9) is located at the rear of the housing 91 and held in place by a locking knob 122. The tube holder secures the fluid tube connected to a micropipette via a hollow shaft pipette Holder (FIG. 9) or connected to a micropipette clamped to a holder 90 on a solid shaft pipette holder 84 (FIGS. 7 and 8). Instead of a micropipette a microelectrode can be used. The outer cylindrical housing 91, the end cap 114 and cone adapter to comprise the body of the inertial impact drill.

From the foregoing description it will be apparent that improved inertial drills, embodying the invention have been described. Variation and modifications of the herein described drills within the scope of the invention will undoubtedly become apparent to those skilled in the art. The foregoing description, therefore, should be taken as illustrative and not in a limiting sense.

What is claimed is:

1. An inertial impact drill having a drilling element for penetration of the walls of biological tissue, an inertial mass movable with respect to the element and coupled mechanically to the element, and means for transmitting mechanical pulses to the element to effect drilling of the tissue without a net displacement of the element.

2. An inertial impact drill per claim 1 that incorporates two opposing electromechanical actuators connected to the mass, which is situated between said actuators.

3. An inertial impact drill per claim 2 in which said actuators each have two electrical contacts.

4. An inertial impact drill per claim 1 in which said actuators are made of a piezoelectric material.

5. An inertial impact drill per claim 1 in which said actuators are made of an electrostrictive material.

6. An inertial impact drill per claim 1 further comprising a body of the drill coupled to the element and to the mass whereby the motion of said inertial mass is transferred to said body generating an impact or a series of impacts in the direction of the major axis of said body, said impact being transferred from said body to said element which is selected from the group consisting of a micropipette and a microelectrode, such that no net displacement in said direction of said micropipette or said microelectrode results.

7. An inertial impact drill per claim 1 in which said means for transmitting pulses comprises means for generating electrical pulses triangular in waveform which are approximate impulse waveforms having broadband frequency content comprised of a plurality of harmonics with frequencies greater than 1 KHz.

8. An inertial impact drill per claim 7 in which said element is mechanically resonant at a frequency an order of magnitude higher than the repetition rate of the pulses whereby the electrical pulses applied to said actuators cause generation of mechanical oscillation at the resonant frequency of said element which is greater than 1 KHz.

9. An inertial impact drill per claim 1 wherein said transmitting means comprises a driver/amplifier.

10. An inertial impact drill per claim 2 further comprising a micromanipulator that provides for positioning and displacement of said drilling element and a drilling mechanism comprising the actuators and the mass.

11. An inertial impact drill per claim 2 in which said actuators are electrically connected in series with one said contact of a first of said actuators connected to a dc reference voltage, one said contact of a second said actuators is connected to a common electrical ground and with second said contacts of both said actuators connected to a common point.

12. An inertial impact drill per claim 11 in which the sum of the voltage drops due to a pulse across the said actuators from said one contact of said first actuator to ground is equal to the magnitude of said dc reference voltage.

13. An inertial impact drill per claim 11 in which said opposing actuators are electrically energized by said dc reference voltage to approximately one half of their maximum strain to achieve mechanical preload of said inertial mass to keep said actuators and bonds between said inertial mass and said actuators in constant compression to facilitate mechanical stability and increase stiffness.

14. An inertial impact drill per claim 2 in which said opposing actuators are mechanically perloaded to further facilitate mechanical stability and increase stiffness.

15. An inertial impact drill per claim 14 in which said bodies of said actuators are pressed against hemispherically shaped bosses thereby providing a single point axial contact.

16. An inertial impact drill per claim 1 in which said transmitting mechanism is operative to provide a sequence containing a plurality of inertial impacts a number of which is a function of the number of said pulses applied to said actuators as controlled by an operator.

17. An inertial impact drill per claim 16 in which the repetition rate, amplitude, and duration of said pulses is controlled by the operator using controls on a driver/amplifier.

18. An inertial impact drill per claim 17 in which said number electrical pulses is controllable by the operator using a foot pedal electrically connected to said driver/amplifier.

19. An inertial impact drill per claim 6 wherein said transmitting means provides for independent control of the repetition rate, amplitude and duration of two independent types of pulses.

20. An inertial impact drill per claim 19 in which two foot pedals are provided to select one of said two independent types of pulses and to control the number of said pulses in said plurality.

21. An inertial drill per claim 1 further comprising an inertial impact drill having a drilling element for penetration of the walls of biological tissue, an inertial mass movable with respect to the element and coupled mechanically to the element, and means for transmitting mechanical pulses to the element to effect drilling of the tissue without a net displacement of the element housing in which said mass is deployed for movement along an axis through said housing, and means for attaching said element to said housing so that it extends generally along said axis and said pulses are transmitted along said axis.

22. The drill per claim 21 wherein said attaching means comprises a snout on said housing at one end thereof and a clamp for said element on a rod attachable to said element on said snout outwardly from said one end.

23. The drill per claim 21 wherein attaching means comprises a hollow snout on said housing at one end thereof, a side wall of said snout having an opening into said snout for entry of said element and passage thereof through said snout at an exit intersect by said axis.

24. The drill according to claim 23 further comprising a collet clamp deposed in said exit through which said element extends and said element is clamped to said snout.

* * * * *